US 11,583,329 B2

(12) United States Patent
Brodbeck et al.

(10) Patent No.: US 11,583,329 B2
(45) Date of Patent: Feb. 21, 2023

(54) CRYOSURGICAL INSTRUMENT

(71) Applicant: Erbe Elektromedizin GmbH, Tuebingen (DE)

(72) Inventors: Achim Brodbeck, Metzingen (DE); Joerg Kronenthaler, Hirrlingen (DE); Marcus Adler, Tuebingen (DE); Hanna Andel, Tuebingen (DE); Klaus Fischer, Nagold (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 228 days.

(21) Appl. No.: 16/051,902

(22) Filed: Aug. 1, 2018

(65) Prior Publication Data

US 2019/0038333 A1 Feb. 7, 2019

(30) Foreign Application Priority Data

Aug. 4, 2017 (EP) .................................. 17184993

(51) Int. Cl.
*A61B 10/04* (2006.01)
*A61B 18/02* (2006.01)
*A61B 18/00* (2006.01)

(52) U.S. Cl.
CPC .......... *A61B 18/0218* (2013.01); *A61B 10/04* (2013.01); *A61B 18/02* (2013.01);
(Continued)

(58) Field of Classification Search
CPC .................... A61B 18/0218; A61B 2018/0212
See application file for complete search history.

(56) References Cited

U.S. PATENT DOCUMENTS

| 4,278,090 A | 7/1981 | Van Gerven |
| 5,423,807 A | 6/1995 | Milder |

(Continued)

FOREIGN PATENT DOCUMENTS

| CN | 1703168 B | 5/2010 |
| CN | 102083381 A | 6/2011 |

(Continued)

OTHER PUBLICATIONS

Extended European Search Report dated Feb. 2, 2018, for European Application No. 17184993.8 (9 pgs.).

(Continued)

*Primary Examiner* — Linda C Dvorak
*Assistant Examiner* — Ryan T Clark
(74) *Attorney, Agent, or Firm* — Fitch, Even, Tabin & Flannery LLP

(57) ABSTRACT

A cryosurgical instrument includes a feed line for conveying fluid into an expansion chamber. The feed line has a capillary line section that terminates in the expansion chamber and forms an aperture for the fluid to undergo the Joule-Thomson effect. The flow cross-section of the feed line decreases in at least one transition section of the feed line in the form of a funnel. Following each transition section there preferably follows a step section, in which latter section the flow cross-section is preferably largely constant. The last step section is preferably formed by the capillary line section. Due to the acceleration of the fluid in the transition sections and the abating of pressure fluctuations in the capillary tube section and, optionally in the additional step sections, the expansion range in the expansion chamber is increased, without impeding the backflow of the expanded gas out of the expansion chamber.

16 Claims, 5 Drawing Sheets

(52) U.S. Cl.
CPC ............... *A61B 2018/00023* (2013.01); *A61B 2018/0212* (2013.01); *A61B 2018/0262* (2013.01); *A61B 2018/0268* (2013.01); *A61B 2018/0293* (2013.01); *A61M 2206/11* (2013.01)

(56) References Cited

U.S. PATENT DOCUMENTS

| | | | |
|---|---|---|---|
| 5,759,182 | A | 6/1998 | Varney et al. |
| 6,106,518 | A * | 8/2000 | Wittenberger ......... A61B 18/02 606/21 |
| 6,270,493 | B1 | 8/2001 | Lalonde |
| 6,503,246 | B1 | 1/2003 | Har-Shai et al. |
| 6,623,479 | B1 | 9/2003 | Nun |
| 6,830,581 | B2 | 12/2004 | Magers |
| 7,422,583 | B2 | 9/2008 | Maurice |
| 7,967,815 | B1 | 6/2011 | Berzak et al. |
| 8,480,663 | B2 | 7/2013 | Ingle et al. |
| 8,591,505 | B2 | 11/2013 | Sharon et al. |
| 2002/0161360 | A1 | 10/2002 | Carroll |
| 2004/0106969 | A1* | 6/2004 | Dobak, III ............. A61B 18/02 607/105 |
| 2005/0016188 | A1 | 1/2005 | Lentz |
| 2005/0288657 | A1 | 12/2005 | Lentz et al. |
| 2011/0071427 | A1* | 3/2011 | Fischer .................. A61B 10/02 600/565 |
| 2011/0245821 | A1 | 10/2011 | Zachman |
| 2012/0130359 | A1 | 5/2012 | Turovskiy |
| 2013/0310822 | A1 | 11/2013 | Mayse et al. |
| 2014/0275767 | A1* | 9/2014 | Baust ..................... A61B 18/02 600/104 |
| 2019/0145363 | A1* | 5/2019 | Gocmen ................ F02M 55/02 72/276 |

FOREIGN PATENT DOCUMENTS

| | | |
|---|---|---|
| CN | 102378600 A | 3/2012 |
| CN | 103402449 A | 11/2013 |
| DE | 2831199 C3 | 1/1981 |
| DE | 69906320 T2 | 8/2003 |
| DE | 102008024946 A1 | 12/2009 |
| EP | 1398002 A1 | 3/2004 |
| JP | H02126840 A | 5/1990 |
| JP | H09-506272 A | 6/1997 |
| JP | H09-511414 A | 11/1997 |
| JP | 2004-511274 A | 4/2004 |
| JP | 2011-520513 A | 7/2011 |
| JP | 2011-520536 A | 7/2011 |
| RU | 2007104705 A | 4/2009 |
| WO | 99/66970 A1 | 12/1999 |
| WO | 00/47118 A1 | 8/2000 |
| WO | 2002002026 A1 | 1/2002 |
| WO | 2006/006986 A2 | 1/2006 |
| WO | 2008/099490 A1 | 8/2008 |

OTHER PUBLICATIONS

Chinese Office Action and Search Report dated Sep. 3, 2020, in corresponding Chinese Application No. 201810878609.7, with English translation (15 pages).

Japanese Office Action dated Sep. 22, 2021, in corresponding Japanese Application No. 2018-137461, with machine English translation (14 pages).

Chinese Office Action dated Oct. 19, 2021, in corresponding Chinese Application No. 201810878609.7, with English translation (15 pages).

Russian Office Action dated May 28, 2021, in corresponding Russian Application No. 2018127663/14(044127), with machine English translation (15 pages).

* cited by examiner

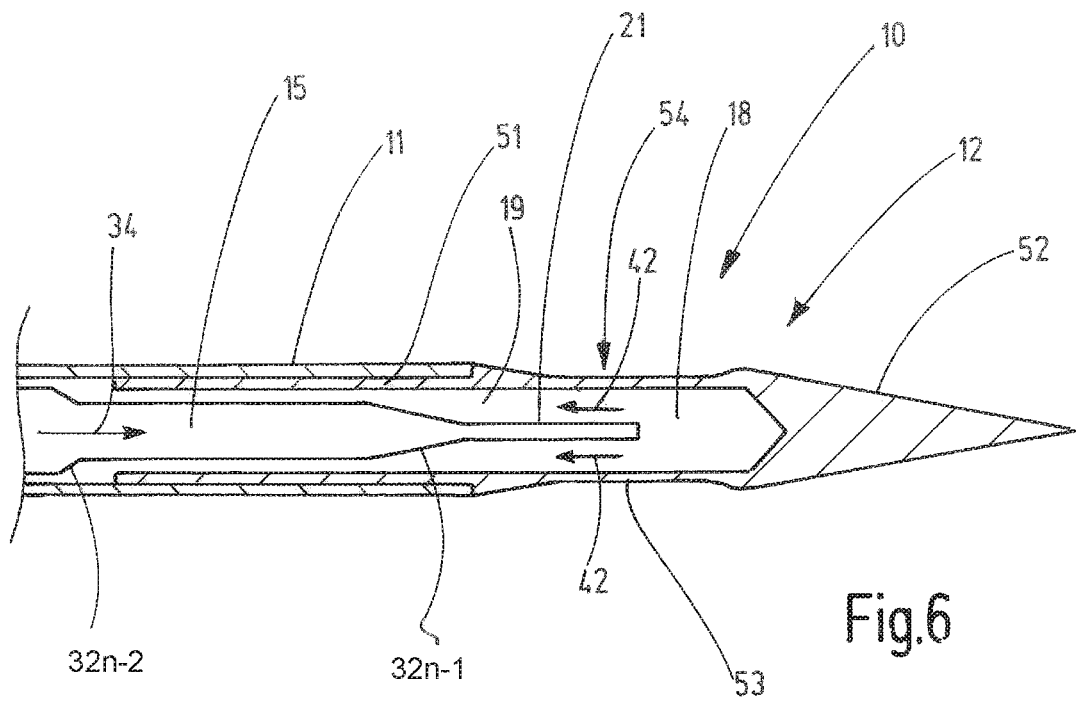
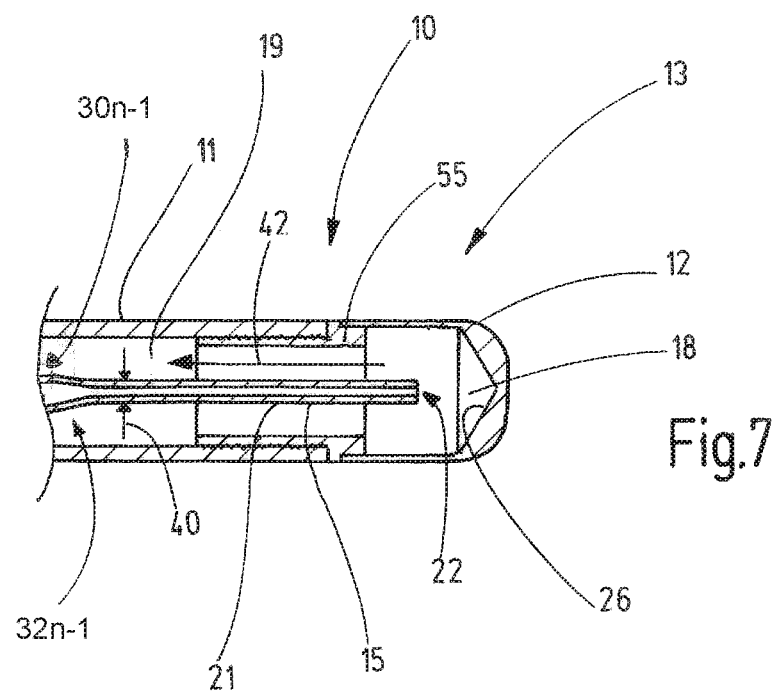

CRYOSURGICAL INSTRUMENT

RELATED APPLICATION(S)

This application claims the benefit of European Patent Application No. 17184993.8, filed Aug. 4, 2017, the contents of which is incorporated herein by reference as if fully rewritten herein.

TECHNICAL FIELD

The invention relates to a cryosurgical instrument that operates under utilization of the Joule-Thomson effect.

BACKGROUND

Prior art has disclosed medical instruments whose working end is being cooled in order to thus generate physiological or therapeutic effects on the tissue of the patient. For example, from publication WO 02/02026 A1 there is known a cryoprobe that comprises a tip for cutting, in which case liquid cooling means is supplied to the tip in order to cool said tip. Publication U.S. Pat. No. 6,830,581B2 describes a heat transfer element to be inserted into a blood vessel, in which case said element is to cool blood in the vessel in that cooled working agent is supplied to the tip of the instrument.

Instruments for cryosurgery work, for example, with the targeted utilization of the Joule-Thomson effect, in which case a fluid experiences a reduction of its temperature due to being slowed down.

Publication DE 10 2008 024 946 A1, for example, discloses a cryosurgical instrument that comprises a feed line for feeding a fluid, in particular a gas, into an expansion chamber in the head of the probe. On the front side of the feed line there is an aperture with an opening through which the fluid flows out of the feed line into the expansion chamber and is thus expanded, whereby the fluid cools. In doing so, the probe tip is cooled. The cooled fluid flows from the probe tip back through a gas feedback line.

Publication WO 2006/006986 A2 describes a cryosurgical instrument comprising a tube with a closed end. Arranged inside the tube there is a gas feed line, to the end of which a capillary tube is connected, in which case the end of the latter terminates in an expansion chamber in the tip of the probe.

Publication US 2012/0 130 359 A1 describes an instrument for cryotherapy with the use of which nerves at the operating site can be affected with cold for therapeutic purposes. The instrument comprises a shaft, at the end of which a working section is provided. Extending through the shaft in the working section, there is a feed line for feeding coolant back into the working section. At the end of the feed line, there may be provided an aperture or a capillary tube with which the feed line terminates in an expansion chamber in the working region.

Publication US 2005/0 016 188 A1 describes an instrument for the cryosurgical ablation of tissue with a cryocatheter comprising a tube having a closed distal end, wherein a feedback line extends in the tube up to the end of the instrument, in which case a capillary tube is arranged in the end of the feed line, said capillary tube terminating in a chamber on the distal end of the instrument.

SUMMARY

It is the object of the present invention to state an improved cryosurgical instrument.

This object is achieved with a cryosurgical instrument described herein that, for example, may be disposed for taking a tissue sample. The cryosurgical instrument according to the invention comprises a feed line for supplying a working fluid, in particular a gas, into an expansion chamber that is preferably arranged on the distal end of the instrument. The feed line has a capillary line section that terminates in the expansion chamber. A return arrangement for returning gas from the expansion chamber is connected to the expansion chamber. The feed line has at least one first section and one second section that form line sections displaying different-size inside cross sections (inside cross-sectional areas). The inside cross-sections determine the flow cross-section for the fluid through the feed line in the first and the second sections. The feed line of the instrument according to the invention is designed in such a manner that the path of flow of the fluid through the feed line tapers in a transition section of the feed line from the first section to the second section in a funnel-shaped manner in the direction toward the expansion chamber. With this funnel-like tapering of the inside cross-section of the feed line in the transition section, it is possible to achieve a stepped progression of the flow cross-section along the feed line with a decrease of the inside cross-section, said decrease being preferably continuous (steady) or step-by-step. As a result of the fact that the inside cross-section of the feed line tapers at least once in a funnel-shaped manner in the direction of flow of the fluid through the feed line in the direction toward the expansion chamber, the fluid is accelerated in the at least one funnel-shaped transition section of the feed line. Due to the funnel-shaped tapering in the transition section the flow cross-section does not decrease suddenly (abruptly) from the flow cross-section of the first section toward the flow cross-section of the second section that is smaller compared to the flow cross-section of the first section. Therefore, due to the funnel shape of the transition-section, pressure fluctuations of the accelerated fluid in the section of the feed line following the funnel-shaped transition section can be largely reduced or prevented.

The instrument according to the invention works, for cooling the working section of the instrument, by utilizing the Joule-Thomson effect that manifests itself on the fluid when the fluid expands in the expansion chamber. Due to the uniform acceleration in the transition section and the use of the capillary line section as the distal end section of the feed line, it is accomplished that the distance over which the fluid particles remain largely together upon exiting from the mouth opening into the expansion chamber is lengthened compared to an instrument that does not comprise the described funnel-shaped taper and capillary line section. In doing so, it can be prevented, in particular, that the jet will widen excessively after the mouth and thus impede the backflow of the gas out of the expansion chamber. As a result of this, the instrument head that contains the expansion chamber and that may contain at least one section of the return system, can be designed in a slim manner. This smoothes the path to obtain miniaturized instrument heads. The use of the capillary line as aperture for the fluid, as well as the largely pressure-surge-free acceleration of the fluid in the at least one transition section in which the flow cross-section tapers in a funnel-shaped manner, in particular, smooth the path to a particularly slim instrument head with which, for example, a safe tissue sample removal can be simplified.

Particularly preferably, the feed line is configured in such a manner that the inside cross-section of the feed line tapers in a funnel-shaped manner in the transition section toward the capillary line section. As a result of this, the fluid can be accelerated and pressure fluctuation at the time of entry into capillary line section can be largely reduced or prevented on entry into the capillary line section, this leading to a large free path length of the fluid, over which length the fluid particles largely remain together upon leaving the capillary line section into the expansion chamber. Preferably, the tapering of the inside cross-section is continuous in a transition region that extends from ahead of the transition section toward the capillary line section—through the transition section and into the capillary line section. The inside wall surface of the feed line in the transition region is preferable free of edges so that, within the transition region along the flow path, there do not exist any sudden changes of the gradient of the inside cross-section.

Preferably, the tapering angle with which the inside cross-section of the feed line tapers at least in the transition section toward the capillary line section in a funnel-like manner is 15° at minimum and 40° at maximum. The tapering angle is included by opposing sections of the inside wall surface of the transition section that determines the flow cross-section through the transition section.

The length of the capillary line section is preferably between a minimum of 1 mm and a maximum of 15 mm. The inside diameter of the capillary line section that determines the flow cross-section of the capillary line section is preferably between a 60 micrometers at minimum and 200 micrometers at maximum.

Preferably, the feed line has at least two transition sections in which the flow path through the feed line tapers in a funnel-shaped manner in the direction of flow toward the expansion chamber.

The first section and the second section preferably form step sections of a series of two, three or more than three step sections of the feed line, wherein a transition section is provided between each two step sections, said transition section being adjacent to the two step sections. As described, the flow cross-section through the at least one transition section, preferably in each transition section, decreases as in a funnel in the direction of the mouth opening of the feed line toward the expansion chamber. The area contents of the inside cross-sectional areas of each step section belong to an inside cross-section step, wherein the area contents of the inside cross-sectional areas of an inside cross-section step of a step section area are greater than the area contents of the inside cross-sectional areas of the inside cross-section step of the step section adjacent—in the direction toward the mouth of the capillary line section downstream—to the same transition section. As a result of this, a stepped progression of the flow cross-section of the feed line up to the mouth of the feed line is provided, in which case the flow path in the transition sections having the funnel-shaped taper is not reduced abruptly—due to the funnel shape—from one cross-section step to the subsequent cross-section step, but is preferably reduced continuously or step-by-step or, in at least one longitudinal section of the transition section, continuously and, in at least another longitudinal section of the transition section, step-by-step in the direction toward the expansion chamber and may advantageously remain largely constant in the step sections along the step sections. The capillary line section may form the last step section of the sequence in flow direction toward the mouth of the last step section. Due to the acceleration in the funnel-shaped transition sections, the fluid particles are imparted with a high speed that carries the fluid jet—upon exiting from the mouth—far into the expansion chamber, as a result of which the expansion range of the fluid is enlarged and the effectiveness of cooling can be improved. Due to the funnel-like taper and the provided step sections, the acceleration of the fluid in the direction toward the expansion chamber—viewed over the course of the sequence—occurs in steps, thereby making possible a reduction of pressure surges and turbulences in the fluid. As a result of this, the range of expansion of the gas in the pressure chamber is enlarged.

During the transition from the mouth opening of the capillary section into the expansion chamber, the flow cross-section for the fluid preferably surges. This promotes a strong formation of the Joule-Thomson effect on the expanding fluid. In addition, a section of the expansion chamber may be available as part of the return system.

The feed line is preferably arranged in the return line, and/or the return line is arranged, for example, next to the feed line. The particularly preferred ratio of the flow cross-section in the return line next to the capillary line section and/or around the capillary line section with respect to the inside cross-section of the capillary line section is greater than or equal to 5.

Preferably, the feed line is configured in such a manner that the outside cross-section (outside cross-sectional area) of the feed line does not decrease abruptly at the funnel-shaped transition sections from the outside cross-section of a step section to the outside cross-section of the step section adjacent to the same transition section but, preferably, decreases continuously or step-by-step or, in at least one subsection of the section of the feed line whose outside cross-section tapers, step-by-step and, in another subsection of the section, continuously in the direction toward the mouth of the capillary line section. Viewed in the direction of flow of the gas flowing away from the expansion chamber following expansion, the outside cross-section of the feed line preferably, accordingly does not increase abruptly but, preferably, continuously and/or step-by-step. If the wall of the feed line, at the same time, forms a wall of the return system, in particular a return line, the return of the gas from the expansion region through the space provided by the outside cross-section reduction can be improved. Different from an abrupt decrease of the outside cross-section of the feed line in the direction toward the mouth, the outside diameter of the flow cross-section for the gas that flows back is not changed abruptly; it is, for example, tapered. As a result of this, the flow resistance of the return system, in particular a return line may be decreased.

The instrument may be configured in such a manner that the flow cross-section of the return line in the direction of flow of the gas during the return away from the expansion chamber decrease, in the transition sections, continuously or step-by-step or, in the transition sections in at least one length section, continuously and, in at least one other length section, step-by-step.

Preferably, at least the section of the feed line having the capillary line section and the transition section adjacent to the capillary line section is configured without seams. This simplifies a reliable process of manufacturing the instrument in order to avoid problems and abrupt changes of the flow cross-section of the feed line up to its mouth. Particularly preferably, at least the section of the feedback line having the capillary line section and the funnel-shaped transition section is configured in one piece without seam, so that a reliable process of producing the transition sections and the capillary line section is simplified.

Overall, the feed line may be manufactured using a rotary swaging process. Preferably, at least the section of the feed line having the capillary line section and the transition section adjacent to the capillary line section are produced by means of a rotary swaging process. Particularly preferably, at least the section of the feed line with the capillary line section and the funnel-shaped transition sections is produced by means of the rotary swaging process. By using the rotary swaging process, it is possible to reliably achieve a high quality with low surface roughness and lower surface waviness of the inside surface of the feed line that determines the flow cross-section.

The wall thickness of the capillary line section may be equal to or less than the wall thickness of the feed line section that is adjacent to the transition section upstream toward the capillary line section. This facilitates the provision of a large space next to the capillary line section or around the capillary line section for the return of the gas from the expansion zone. In addition, the heat transfer between the gas returned next to or around the capillary line section and the gas supplied through the capillary line section can be increased.

The ratio of the inside diameter of the capillary line section with respect to the length of the capillary line section is preferably between 0.004 at minimum to 0.2 at maximum.

Preferably, the mouth opening of the capillary line section through which the fluid exits from the feed line and enters into the expansion chamber is located on the front side of the capillary line section. Preferably, the jacket of the capillary line section that encloses the lumen of the capillary line section and that conveys the fluid is free of lateral openings.

The distance between the mouth opening and the opposing wall surface of the expansion chamber, said wall delimiting the lumen of the expansion chamber, is preferably between 0.5 mm at minimum and 5 mm at maximum.

BRIEF DESCRIPTION OF THE DRAWINGS

Further advantageous features of the cryosurgical instrument according to the invention can be inferred from the dependent claims, as well as from the description hereinafter and the figures. They show in FIG. 1—a detail, in longitudinal sectional view, of a distal end of a cryosurgical instrument according to prior art, FIG. 2a—a detail, in longitudinal sectional view, of an exemplary cryosurgical instrument according to the invention, FIGS. 2b to 2d—views of cross-sections of the instrument according to the invention depicted in FIG. 2a, on the section planes shown in FIG. 2a, FIG. 3—a detail, in longitudinal sectional view, of an exemplary cryosurgical instrument according to the invention, FIG. 4—a detail, in longitudinal sectional view, of a cryosurgical instrument according to another exemplary embodiment, FIG. 5—a detail, in longitudinal sectional view, of an exemplary cryosurgical instrument according to the invention guided in the working channel of an endoscope, FIG. 6—a detail, in longitudinal sectional view, of an exemplary instrument according to the invention, and FIG. 7—a detail, in longitudinal sectional view, of an exemplary instrument according to the invention.

DETAILED DESCRIPTION

Figure 1:
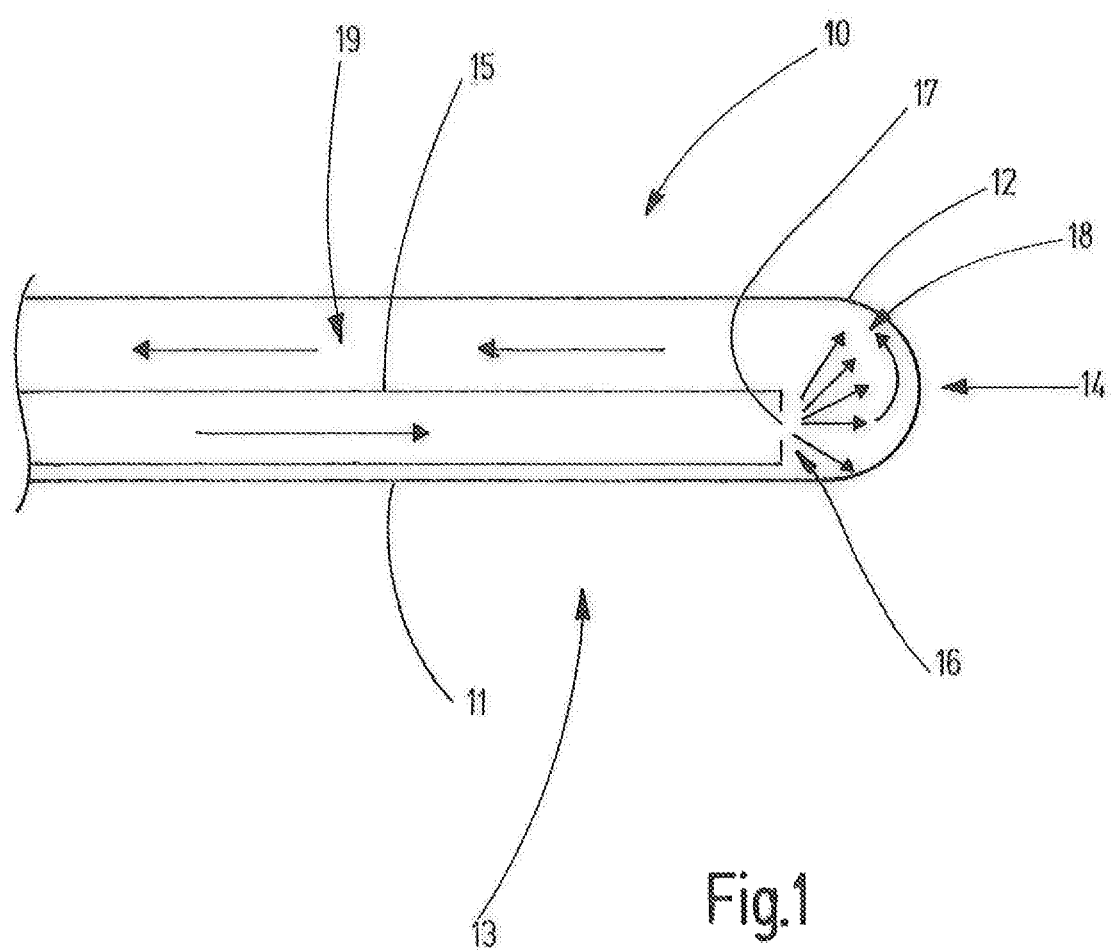

FIG. 1 is a longitudinal sectional view of a distal end section 13 of a prior-art cryosurgical instrument 10. The instrument 10 has a shaft 11 that extends up to a head 12 of the instrument 10 on the distal end 13a of the instrument 10. Outside, on the head 12, there is provided an adhesion surface 14 where a tissue sample can attach frozen for removal. Inside the shaft 11 there is arranged a feed line 15 for supplying gas to the distal end 13a of the instrument 10. The feed line 15 ends with an aperture 16 having an opening (mouth) 17, through which the gas may flow out of the feed line 15 into an expansion chamber 18 in the head 12 of the instrument 10. When the gas stream from the feed line 15 is decelerated at the aperture 16 and the gas expands downstream of the aperture 16 upon entering into the expansion chamber 18, the Joule-Thomson effect will become apparent on the gas in that the expanded gas in the expansion chamber 18 experiences a temperature reduction. Consequently, said gas is able to cool off the head 12 of the instrument 10 having the adhesion surface 14. The cooled gas leaves the expansion chamber 18 through a return line 19 that is arranged in the shaft 11 next to the feed line 15. The flowback of the gas out of the expansion chamber 18 into the return line 19 can—as is indicated by arrows in FIG. 1—be impeded by the gas flowing out of the mouth opening 17. Therefore, a relatively large expansion chamber 18 must be provided in order to be able to ensure a suitable backflow.

Figure 2A:
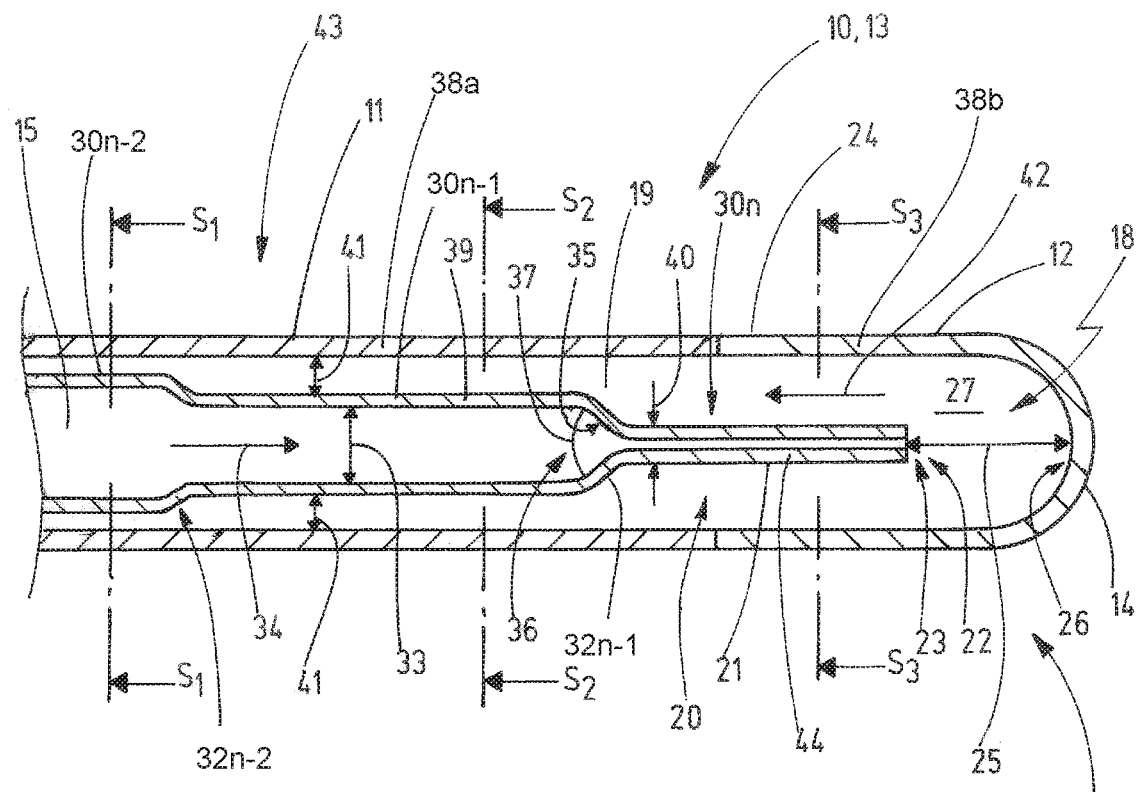

FIG. 2a shows a longitudinal section of a cryosurgical instrument 10 according to the invention. In the cryosurgical instrument 10 according to the invention the distal end 20 of the feed line 15 is formed by a capillary line section (21) (capillary tube section). The capillary line section 21 has a mouth 22 into the expansion chamber 18 on the front side 23 of the capillary line section 21. The capillary line section 21 extends up to and into the head 12 of the instrument 10 that is formed by a cap 24 that encloses the expansion chamber 18. The distance 25 between the mouth opening 22 of the capillary line section 21 and the opposing wall surface 26 of the cap 24 that delimits the expansion chamber 18 is preferably 0.5 mm at minimum up to 5 mm at maximum. The wall surface 26 of the cap 24 opposite the mouth 22 of the capillary tube section 21, said section delimiting the lumen 27 of the expansion chamber 18, may be—as shown—for example a spherical cap surface 26 that is disposed and arranged to convey gas impinging on the wall surface 26 of the cap 24 into the feedback line 19.

The capillary line section 21 forms the n-th step section $30n$ of a series of at least n=2, preferably n>2, for example, and as shown in FIG. 2a, $n=3$ step sections $30n$-2, $30n$-1, $30n$ of the feed line 15. Arranged between two step sections $30n$-2, $30n$-1, $30n$ of the feed line 15, there is respectively one transition section $32n$-2, $32n$-1 adjacent to the two step sections $30n$-2, $30n$-1 or $30n$-1, $30n$, respectively. In at least one transition section $32n$-2, $32n$-1 the inside cross-sectional area 33 of the feed line 15 decreases preferably funnel-like, for example conically, in distal direction 34 toward the mouth 22 of the capillary line section 21, so that when the instrument 10 is loaded with a fluid, for example a gas, an acceleration of the fluid flowing through the feed line 15 toward the mouth 22 will occur in the transition sections $32n$-2, $32n$-1. The inside wall surface 35 of the transition section $32n$-1 adjacent to the capillary tube section 21 preferably has essentially no surface sections perpendicular to the flow direction 34 of the gas, against which the gas flowing through the transition section in flow direction 34 toward the expansion chamber 18 would have to flow. Preferably, the same applies to each of the remaining transition sections $32n$-1. Rather, the depicted exemplary transition section $32n$-1 toward the capillary tube section 21 has an inside wall surface 35 that is inclined relative to the direction of flow 34—viewed in longitudinal section through the transition section $32n$-1—wherein their circumferential sections include acute angles smaller than 90° with the direction of flow 34. The remaining transition sections 32*n*-2 are preferably configured in the same way. FIG. 2*a* shows a funnel-shaped transition section 32*n*-2 toward the next to last step section 30*n*-1 and a funnel-shaped transition section 32*n*-1 toward the capillary line section 30*n* that forms the last step section 30*n* of the sequence. Preferably, the flow path tapers continuously in a transition region 36 from before the transition section 32*n*-1 to the capillary line section 30*n*, 21, through the transition section 32*n*-1 in the capillary line section 21. Preferably, there are—in the transition region 35 in the flow path in the feed line 15—in particular no inside wall surfaces of the feed line 15 perpendicular to the direction of flow 34 that would lead to an abrupt change of the flow cross-section. Preferably, the flow cross-section of the feed line 15 decreases in each transition section 32*n*-2, 32*n*-1 of the feed line 15 between the step sections 30*n*-2, 30*n*-1, 30*n* in a funnel-shaped manner in the direction of flow 34 in the direction toward the mouth 22, so that, preferably, a series of alternatingly arranged step sections 30*n*-2, 30*n*-1, 30*n* and transition sections 32*n*-2, 32*n*-1 having a funnel-shaped inside tapering cross-section are formed.

It is advantageous when the flow cross-section in the transition section(s) 32*n*-2, 32*n*-1 of the feed line 15 does not decrease abruptly from the flow cross-section in the step section 30*n*-2 or 30*n*-1 of the feed line 15, said step section being arranged in front of the transition section 32*n*-2 or 32*n*-1 and being adjacent to the transition section 32*n*-2 or 32*n*-1, toward the flow cross-section in the step section 30*n*-1 or 30*n* of the feed line 15, said section being adjacent to the transition section 32*n*-2 or 32*n*-1 in the flow path in the transition section(s) 32*n*-2, 32*n*-1, but when the flow path in the transition section(s) 32*n*-2, 32*n*-1 tapers beyond a path section of the flow path toward the mouth 22. It is this that reduces any eddying of the fluid and the pressure fluctuations of the fluid in the step section 30*n*-1, 30*n* of the feed line 15 following the transition section 32*n*-2 or 32*n*-1.

The tapering angle 37 of the inside cross-section 33 in the transition section 32*n*-1 toward the capillary tube section 21, 30*n* is preferably 15° at minimum to 40° at maximum. The tapering angle 37 is determined by the inside wall surface 35 of the transition section 32*n*-1 that laterally delimits the flow cross-section through the transition section 32*n*-1. The inside wall surface 35 of the transition sections 32*n*-2, 32*n*-1—viewed in longitudinal section through the feed line 15 along the direction of flow 34—is preferably arranged inclined with respect to the direction of flow 34. The inside wall surface 35 may be, for example, the lateral surface of a truncated cone or a truncated pyramid. The transition section 32*n*-2 toward the next to last step section 30*n*-1 and/or the transition section 32*n*-1 toward the capillary line section 21 may be symmetrical relative to a plane parallel to the direction of flow 34. The centers of the flow cross-sectional areas in the transition section 32*n*-2 toward the next to last step section 30*n*-1 and/or the centers of the flow cross-sectional areas in the transition section 32*n*-2 in the transition section 32*n*-1 on the capillary line section 21 can be located—as in a symmetrical funnel—on a straight line that extends perpendicularly to the flow cross-sectional area in the inlet in the respective transition section 32*n*-1, 32*n*-2. As an alternative to a symmetrical funnel-shaped tapering of the flow cross-section in one or more transition sections 32*n*-2, 32*n*-1, the flow cross-section of the transition section 32*n*-2 may taper toward the next to last step section 30*n*-1 and/or the transition section 32*n*-1 toward the last step section 30*n*, for example as in an asymmetrical funnel.

The step sections 30*n*-2, 30*n*-1, 30*n* define the inside cross-sectional steps. In a step section 30*n*-2, 30*n*-1, 30*n*, the inside cross-sections belong to an inside cross-sectional step. Inside each step section 30*n*-2, 30*n*-1, 30*n* the inside cross-section of the feed line 15 remains within a specific size range (step). Within a step section 30*n*-1, 30*n*, the flow cross-section may be constant, for example. The inside cross-sections in the size range of a step section 30*n*-2, 30*n*-1 are greater than the inside cross-sections in the size range of the respectively downstream (toward the mouth) step section 30*n*. The feed line 15 displays, accordingly, not a surge-like stepped progression of the inside cross-section between the steps in the transition sections 32*n*-2*m* 32*n*-1, but, preferably displays a continuous or step-by-step transition of the flow cross-section to the next step. It is also possible that the flow cross-section tapers step-by-step in at least in one transition section 32*n*-2, 32*n*-1 in at least one first longitudinal section of the transition section 32*n*-2, 32*n*-1 and continuously in at least one other longitudinal section of the transition section 32*n*-2, 32*n*-1 that is located upstream or downstream of the first longitudinal section, so that the flow cross-section in the transition section 32*n*-2, 32*n*-1 overall tapers continuously and step-by-step toward the next step. In particular, the feed line 15 may be configured in such a manner that the inside cross-section of the feed line 15 decreases monotonously from the start of the series of step sections 30*n*-2, 30*n*-1, 30*n* in the direction of flow 34 up to the mouth 22 of the feed line 15. This means that the inside cross-section decreases—at least in some sections—strictly monotonously and may optionally remain the same in some sections.

In one embodiment, the inside wall surface 35 of the feed line 15 in the transition section 30*n*-1 toward the capillary line section 21, into the capillary line section 21 up to the mouth of the feed line 15, may be free of edges or bends oriented transversely with respect to the direction of flow 34 through the feed line 15, said edges or bends potentially meaning an abrupt change of the gradient of the flow cross-section of the feed line 15.

Next to the feed line 15 and/or around the feed line 15, there is preferably formed the flow cross-section of the return line 19. In the depicted exemplary embodiment, the feed line 15 is arranged, at least in some sections, in the return line 19. The flow cross-section of the return line 19 is delimited, on the one hand, by the wall 38*a* of the shaft as well as the wall 38*b* of the head 12, and on the other hand, by the wall 39 of the feed line 15. In FIG. 2*a*, the feed line 15 is shown as being arranged coaxially in the shaft 11 and the cap 24. However, the feed line 15, as well as the shaft 11 and/or the cap 24, may be non-coaxial, i.e., preferably have parallel center axes.

Preferably, the outside cross-section 40 of the feed line 15 in the transition sections 32*n*-2, 32*n*-1, as illustrated, does not decrease abruptly in the direction 34 toward the mouth 22 but, preferably, continuously or step-by-step. In at least one transition section 32*n*-2, 32*n*-1 the outside cross-section of the feed line 15 may decrease continuously in longitudinal sections and step-by-step in longitudinal sections—in the direction toward the mouth 22. As a result of this, the flow cross-section 41 of the return line 19—as shown by the exemplary embodiment according to FIG. 2*a*—can decrease in the transition sections 32*n*-2, 32*n*-1 in the direction 42 of the gas flowing from the expansion chamber 18 through the return line 19, respectively along the length of the transition sections, i.e., not abruptly from the flow cross-section ahead of the transition section 32*n*-2, 32*n*-1 to the flow cross-section after this transition section 32*n*-2, 32*n*-1. The flow cross-section 41 of the return line 19 may decrease, in particular, continuously or step-by-step, or, in longitudinal sections, continuously and—in the direction of flow 42 of the gas flowing away from the expansion chamber 18 in the transition sections 32n-2, 32n-1, in particular—in a continuous or step-by-step manner, or continuously in longitudinal sections and step-by step in longitudinal sections. The flow cross-section 41 of the return line 19 next to the capillary tube section 21, 30n or around the capillary tube section 21, 30n and/or between the transition sections 32n-2, 32n-1 may largely be constant.

Preferably, the step sections 30n-2, 30n-1, 30n determine the outside cross-section steps. In one step section 30n-2, 30n-1, 30n the outside cross-sections (outside cross-sectional areas) of the feed line 15 belong to one outside cross-section step. Within each step section, the outside cross-section of the feed line remains within a specific size range (step). Along one step section 30n-2, 30n-1, 30n the outside cross-sections of the step section 30n-2, 30n-1, 30n, may be constant, for example. The outside cross-sections in the size range of one step section 30n-2, 30n-1 are greater than the outside cross-sections in the size range of the respectively downstream (toward the mouth) following step section 30n-1, 30n. Accordingly, the feed line 15 shows preferably a stepped progression of the outside cross-section displaying—between the steps in the transition sections 32n-2, 32n-1—a non-abrupt transition of the outside cross-section toward the next step. Rather, the transition extends preferably over the length of the transition section 32n-2, 32n-1 and/or the transition of the outside cross-section toward the next step is preferably continuous, or occurs—viewed from the flowing fluid—step-by-step. The outside cross-section of the feed line 15 between the transition sections 32n-2, 32n-1 shown by FIG. 2c and between the transition section 32n-1 toward the capillary line section 21 and the mouth 22 is preferably mostly constant, so that the capillary line section 21 displays a largely constant outside cross-section along the longitudinal extent of the capillary line section 21.

Figures 2B, 2C, 2D:
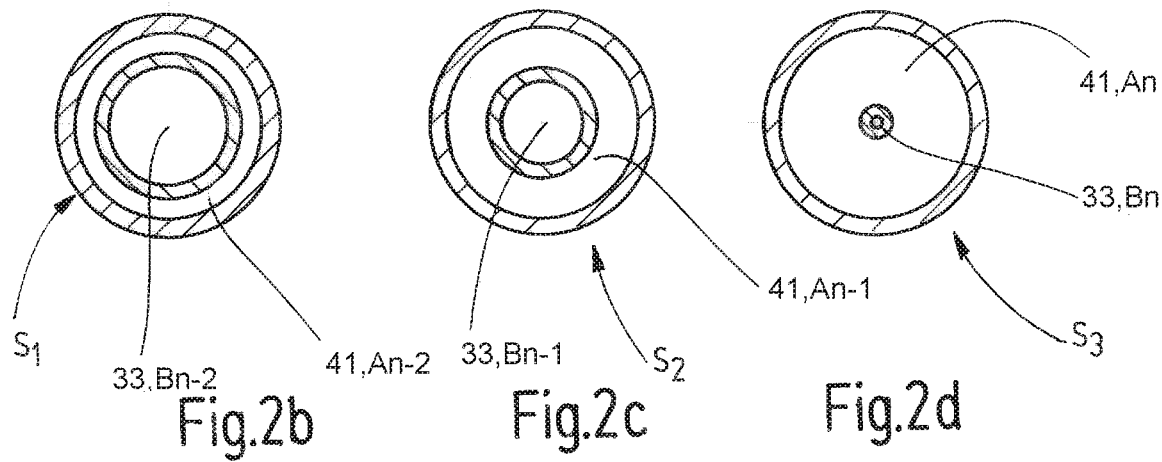

As can be seen with reference to FIGS. 2b to 2d, referring to the exemplary embodiment depicted by FIG. 2a, the ratio of the flow cross-sectional area content 41 (An-2, An-1, An) of the return line 19 next to a step section 30n-2, 30n-1, 30n or around a step section 30n-2, 30n-1, 30n increases—due to the formation of the feed line 15 in the shaft 11—toward the inside cross-sectional area content 33 (Bn-2, Bn-1, Bn) in the step section 30 in the direction of flow 34 toward the mouth 22 from step section to step section, meaning that said ratio is greatest in the capillary line section 21. Thus, analogously, An:Bn≥An-1:Bn-1≥An-2:Bn-2, applies.

Figure 3:
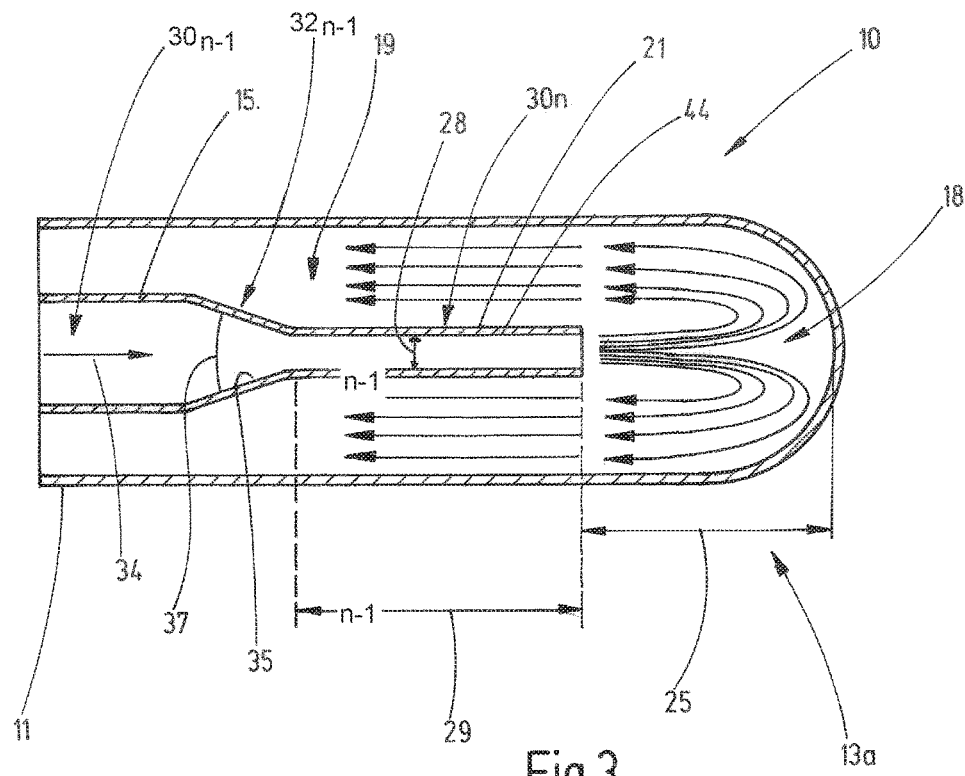

The ratio of the area content of the flow cross-section of the return line 19 next to the capillary line section 21 and/or around the capillary line section 21 with respect to the area content of the flow cross-section of the capillary line section 21 is preferably greater than or equal to 5. The inside diameter 28 (for purposes of clarity, drawn in an exemplary manner in FIG. 3) of the capillary line section determines the flow cross-section 33 of the capillary line section. The ratio of the inside diameter 28 of the capillary line section 21 with respect to the length (for purposes of clarity, drawn in an exemplary manner in FIG. 3) of the capillary line section 21 is preferably between 0.004 at minimum and 0.2 at maximum. The length 29 of the capillary tube that forms the capillary line section 21 may be, for example between 1 mm at minimum and 15 mm at maximum. The inside diameter 28 of the capillary line section 21 may be, for example, 60 micrometers at minimum and 200 micrometers at maximum.

The section of the feed line 15 having the transition sections 32n-2, 32n-1, the step section 30n-1 between the transition sections 32n-2, 32n-1 and the capillary line section 21, 30n is preferably formed without seams in one piece. For example, the section can be made by using the rotary swaging process. The cap 24 of the shaft forming the head 12 having the adhesion surface 14 may consist of stainless steel, for example. For example, the shaft 11 may consist of PEEK, PA, PUR or PTFE. The shaft 11 may be rigid or flexible.

During operation of the cryosurgical instrument 10, the following takes place:

With the use of a fluid source (not illustrated) connected to the feed line 15, the feed line 15 is loaded with a fluid, in particular gas, for example $N_2O$ or $CO_2$, in which case the fluid flows on the distal working end 43 of the cryosurgical instrument 10 from a tube-shaped step section 30n-2, 30n-1, 30n through the adjacent transition section 32n-2, 32n-1 in the direction of the mouth 22 and the expansion chamber 18 into the subsequent tube-shaped step section 30n-2, 30n-1, 30n. Due to the funnel-like decrease of the inside cross-section 33 and thus the flow cross-section of the feed line 15 in the transition sections 32n-2, 32n-1 in the direction of the expansion chamber 18, the fluid is accelerated in the transition sections 32n-2, 32n-1. Due to the reduction that is not abrupt in the transition sections but—extending over a certain length—preferably continuous or step by step of the flow cross-section 33 from step to step, eddying and/or pressure fluctuations in the step section 32n-2, 32n-1 due to accelerations in each transition section 32n-2, 32n-1 are largely prevented. Preferably, the step sections 30n-2, 30n-1, 30n each have one length, so that eddies and/or pressure fluctuations in step the section 30n-2, 30n-1, 30n following the transition section 32n-2, 32n-1 abate largely or completely. The gas flows from the (n−1)st step section through the (n−1)st transition section into the capillary tube section 21 (nth step section). Potential pressure fluctuations in the gas due to the transition from the (n−1)st step section to the capillary tube section 21 preferably abate completely due to the formation of the capillary tube section 21. In the capillary tube section 21, there results a laminar flow in the direction of flow 34 toward the mouth 22 exhibiting the corresponding velocity profile that—due to the abating of the pressure fluctuations in the capillary tube section 21 in the distal end section of the capillary tube section 21 adjacent to the mouth opening 22 preferably does no longer change in the direction of flow 34 (undisturbed flow profile). The capillary tube section 21 forms the aperture for the gas for the formation of the Joule-Thomson effect. Therefore, an aperture 16—as in prior art according to FIG. 1—that results in a large widening of the fluid jet when flowing out of the feed line 15 into the expansion chamber 18 and thus leads to a strong interaction with the flowing back gas can thus be omitted as illustrated by FIG. 2a. The gas stream flows out of the capillary tube section 21 into the expansion chamber 18 and, due to the acceleration in the transition sections 32n-2, 32n-1 and the absence of pressure fluctuations before flowing out of the mouth 22, far into the expansion chamber 18 in the direction of the opposing wall surface 26 of the instrument head 12. In doing so, the gas flows out of the mouth 22 largely unimpeded by the flowing back gas. The gas that flows out of the mouth 22 and expands in the expansion chamber 18 experiences a temperature reduction as a result of the Joule-Thomson effect and cools down the head 12 and the adhesion surface 14 in such a manner that a tissue sample can freeze to the adhesion surface 14.

Thereafter, the tissue sample can be separated and removed from the remaining tissue by pulling the instrument 10.

Accordingly, the backflow of the cooled gas is not impeded by the out-flowing gas. The expanded gas from the expansion chamber rather preferably flows parallel to the fluid leaving the feed line 21 through the mouth opening 22 into the expansion chamber 18 in the opposite sense of flow direction out of the expansion chamber 18 into the return line 19. This large-volume back flow is illustrated by arrows in FIG. 3 that shows a detail of the instrument 10 on its distal end 13a. The gas flowing back through the return line 19 slides past the outside wall surface of the capillary tube section 21 of the feed line 15 and withdraws heat from the gas flowing through the capillary line section 21. This is promoted in that the wall 44 of the capillary tube section 21 is preferably as thin as the wall of the step section 30n-1 that is adjacent to the transition section 32n-1 toward the capillary tube section 21, or even thinner.

The backflowing gas may escape through lateral openings (not shown) in the shaft 11, for example.

Figure 4:
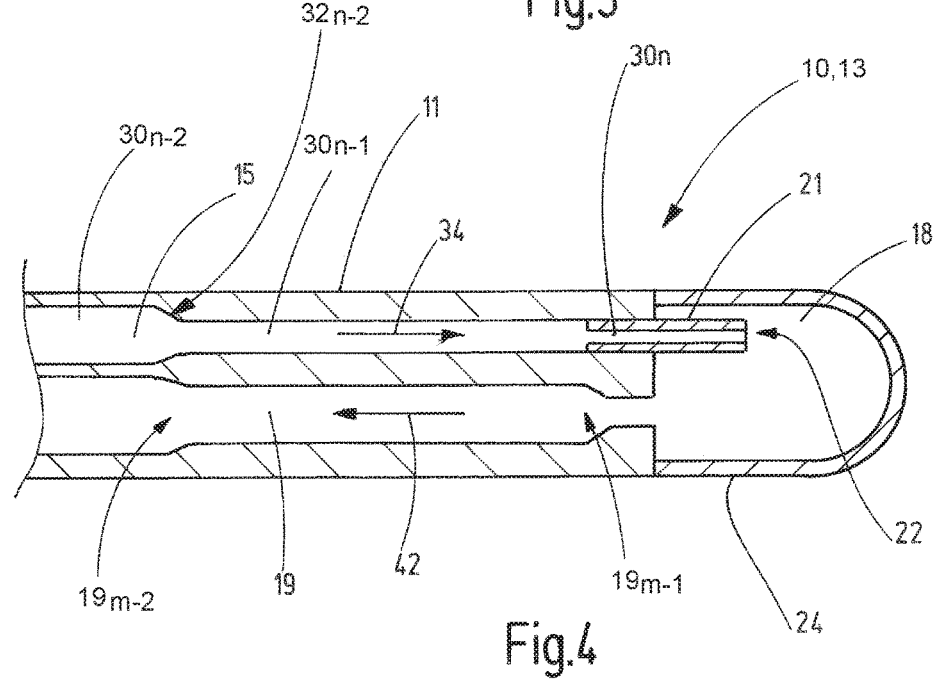

FIG. 4 shows a detail of a modified exemplary embodiment of the instrument 10 according to the invention. Shown is an end section 13 of the instrument 10.

The feed line 15 and the return line 19 are formed next to each other in the shaft 11 of the instrument 10. The capillary tube section 21 of the feed line 15 is inserted in the section of the feed line 15 provided in the shaft 11. The capillary tube section 21 reaches into the cap 24 of the instrument 10, said cap enclosing the expansion chamber 18.

The feed line 15 has at least three step sections 30n-2, 30n-1, 30n, wherein the last step section 30n is formed by the capillary tube section 21. At least in the transition section 32n-2 on the next to last step section 30n-1, the inside cross-section of the feed line 15 decreases in a funnel-shaped manner in the direction toward the mouth 22 in the expansion chamber 18 in the shape of a funnel.

The flow cross-section of the return line 19 connected to the expansion chamber 18 in the shaft 11 decreases in the transition sections 19m-2, 19m-1 of the return line 19 in the form of a funnel. Between the transition sections 19m-2, 19m-1 of the return line 19, the flow cross-section in the return line 19 is preferably largely constant. The number of transition sections 19m-2, 19m-1 of the return line 19 may correspond to the number of transition sections 32n-3, 32n-2, 32n-1 in the feed line 15.

Figure 5:
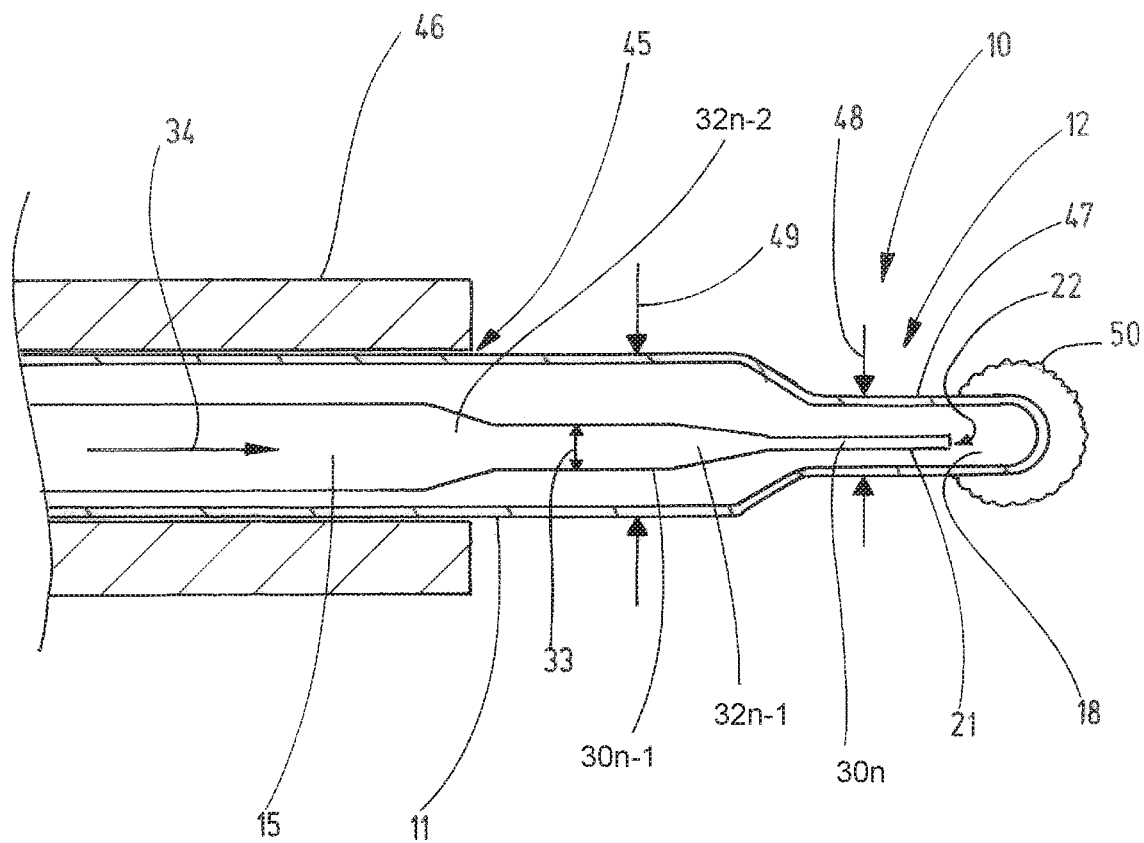

FIG. 5 shows a cryosurgical instrument 10 according to the invention whose shaft 11 is movably guided in longitudinal direction in a working channel 45 of an endoscope 46. On the distal end of the shaft 11 of the instrument 10, the head 12 of the instrument 10 is arranged with a slim distal end section 47, in which case the outside diameter 48 of the end section 47 is reduced relative to the outside diameter 49 of the shaft section adjacent to the head 12. The capillary tube section 21 extends, in the narrow end section 47, into the expansion chamber 18, said chamber being delimited by the end section 47. In the exemplary embodiment, the fluid is accelerated in at least two successive transition sections 32n-2, 32n-1 of the feed line 15 with respectively funnel-shaped reductions of the inside cross-section 33 in the direction of flow 34 toward the mouth 22 in the expansion chamber 18, in which case a tube-shaped step section 30n-1, 30n follows each transition section 32n-2, 32n-1. The distally last step section 30n is the capillary tube section 21. Due to the uniform acceleration in the transition sections 32n-2, 32n-1 and due to the abatement of pressure fluctuations in the capillary tube section 21—so that the flow profile of the fluid flowing through the feed line 15 is preferably constant at the end of the capillary tube section 21, i.e., does no longer change in the direction of flow 34—the fluid will flow, after leaving the mouth 22, far into the expansion chamber 18. As a result of this, a suitable return of the expanded gas out of the expansion chamber 18 without impediment due to the gas flowing out of the mouth 22 into the expansion chamber 18 is possible, despite the confined spatial conditions due to the slim end section 47 of the instrument head 12. Now a tissue sample 50 can be taken with the instrument head 12, said sample having a diameter that is smaller than the diameter of the working channel 45 of the endoscope 46. Consequently, the head 12 of the instrument 10 with the tissue sample 50 can be retracted into the working channel 45 of the endoscope, i.e., after the tissue sample 50 has been taken, so that the tissue sample 50 in the working channel 45 of the endoscope 46 can be removed in a protected manner from the body of the patient.

FIG. 6 shows a detail of an instrument 10 according to the invention with a head that can be mounted with a tube-shaped mounting section 51 to the shaft 11 of the instrument 10. The head 12 has a pointed end section 52, and, between the end section 52 and the mounting section 51, there is arranged a tube-shaped adhesion section 53. The head 12 has a waist 54 on the adhesion section 53. In particular, the outside diameter of the adhesion section 53 is reduced relative to the outside diameter of the pointed end section 52. Preferably, the wall of the adhesion section 53 displays a reduced thickness compared to the wall of the mounting section 51. The adhesion section 53 delimits the expansion chamber 18 that may extend up into the pointed end section 52. The capillary line section 21 of the feed line 15 extends into the adhesion section 53. The pointed end section 52 facilitates the puncturing the tissue for taking the sample. For taking the sample, the feed line 15 of the instrument 10 is loaded with fluid, in which case the fluid flows through the feed line 15 in the direction of flow toward the expansion chamber 18 and expands in the expansion chamber and cools the head 12. In doing so, the freezing effect on the tissue may originate from the adhesion section 53, in particular. The taking of the sample is simplified because, due to the reduced outside diameter of the adhesion section 53 compared to the outside diameter of the pointed end section 52, there is formed a positive connection between the head 12 and the frozen, attached tissue.

FIG. 7 shows a detail of the distal end 13 of an exemplary embodiment of the instrument 10 according to the invention with a head 12 that is mounted to the shaft 11 by means of a head-receiving part 55. The head-receiving part 55 of the instrument 10 extends inside the lumen that is enclosed by the shaft 11 and the head 12. The outside diameter of the capillary line section 21 is smaller than the outside diameter of the step section 30n-1 adjacent to the transition section 32n-1 toward the capillary line section 21. Due to the continuous tapering of the inside cross-section of the feed line 15 in the transition section 32n-1 toward the capillary line section 21, an impediment of the backflow of the expanded gas by the fluid flowing out of the feed line 15 is largely prevented. In addition, the flow resistance of the return line 19 can be improved due to the continuous increase of the outside cross-section 40 of the feed line 15 in the transition section 32n-1 (in the direction of flow of the gas flowing away from the expansion chamber 18) compared to an instrument with abrupt increase. Due to the configuration of the feed line 15, thus—despite the reduction of the free volume through the head-receiving part 55—a suitable return of the expanded gas is made possible. The wall surface 26 opposite the mouth 22 of the capillary tube section 21 and delimiting the expansion chamber 18 is the lateral surface of a cone—in this exemplary embodiment and also in the embodiment according to FIG. 6.

Disclosed herein is a cryosurgical instrument 10 that comprises a feed line 15 for conveying fluid into an expansion chamber 18 of the instrument 10. The feed line 15 has a capillary line section 21 that terminates in the expansion chamber 18 and that forms an aperture for the fluid to form the Joule-Thomson effect during the expansion of the fluid in the expansion chamber 18. The flow cross-section of the feed line 15 decreases in at least one transition section 32n-2, 32n-1, preferably in two or more transition sections 32n-2, 32n-1, of the feed line 15 in the form of a funnel in the direction of flow 34 toward the expansion chamber 18. Following each transition section 32n-2, 32n-1—viewed in the direction of flow 34—there preferably follows, adjacent to the transition section 32n-2, 32n-1, a step section 30n-1, 30n of the feed line 15, in which latter section the flow cross-section is preferably largely constant. The last step section 30n-1, 30n is preferably formed by the capillary line section 21. Pressure fluctuations in the fluid can abate in the step sections 30n-1, 30n. Due to the acceleration of the fluid in the transition sections 32n-2, 32n-1 and due to the abating of pressure fluctuations in the capillary tube section 21 and, optionally in the additional step sections 30n-1, 30n-2, the expansion range in the expansion chamber 18 is increased, without impeding the backflow of the expanded gas out of the expansion chamber 18.

Due to the use of the capillary tube section 21, as well as the funnel-shaped transition section(s) 30n-2, 30n-1, the free path length of the fluid jet is greatly increased without widening the fluid jet in the instrument 10 according to the invention compared to a cryosurgical instrument having an aperture at the end of the feedback line 15, so that the interaction between the fluid flowing from the mouth opening 22 away into the expansion chamber 18 and the gas flowing back from the expansion chamber 18 can be greatly reduced. Preferably, the pressure fluctuations and/or eddies of the fluid flowing through the feed line 15 in the direction toward the mouth 22 abate in one embodiment of the instrument 10 according to the invention in the capillary tube section 21 to such an extent that they no longer define the free path length of the fluid jet without widening in the expansion chamber 18. The free path length of the fluid jet without widening is measured from the mouth opening 22 in the direction of flow 34 of the fluid up to the point in the expansion chamber 18 at which the fluid jet diameter exceeds a size that is equal to the size of the outside diameter of the capillary line section 21 at the mouth opening 22, or the free path length of the fluid jet without widening is measured from the mouth opening 22 in the direction of flow 34 of the fluid up to the point in the expansion chamber 18 at the level (in flow direction 34) where an interaction of the fluid jet flowing away from the mouth opening 22 into the expansion chamber 18 with the gas flowing back to the feedback line 19 sets in.

List of Reference Signs:

| | |
|---|---|
| 10 | Instrument |
| 11 | Shaft |
| 12 | Head |
| 13 | Distal end section of the instrument |
| 13a | Distal end of the instrument |
| 14 | Adhesion surface |
| 15 | Feed line |
| 16 | Aperture |

-continued

List of Reference Signs:

| | |
|---|---|
| 17 | Opening |
| 18 | Expansion chamber |
| 19 | Return line |
| 19m-2, 19m-1 | Transition sections of the return line |
| 20 | Distal end of the return line |
| 21 | Capillary line section/capillary tube section |
| 22 | Mouth |
| 23 | Front side |
| 24 | Cap |
| 25 | Distance |
| 26 | Wall surface |
| 27 | Lumen |
| 28 | Diameter |
| 29 | Length |
| 30n-2, 30n-1, 30n | Step section |
| 32n-2, 32n-1 | Transition section |
| 33 | Inside cross-sectional area/flow cross-sectional area |
| 34 | Direction of flow toward the expansion chamber |
| 35 | Inside wall surface |
| 36 | Transition region |
| 37 | Tapering angle |
| 38a | Wall of the shaft |
| 38b | Wall of the head |
| 39 | Wall of the feed line |
| 40 | Outside cross-section |
| 41 | Flow cross-section of the return line |
| 42 | Direction of flow away from the expansion chamber |
| 43 | Distal working end |
| 44 | Wall of the capillary tube section |
| 45 | Working channel |
| 46 | Endoscope |
| 47 | End section |
| 48 | Outside diameter of the end section |
| 49 | Outside diameter of the shaft |
| 50 | Tissue sample |
| 51 | Mounting section |
| 52 | End section |
| 53 | Adhesion section |
| 54 | Waist |
| 55 | Head-receiving part |
| An-2, An-1, An | Flow cross-sectional area content of the return line |
| Bn-2, Bn-1, Bn | Flow cross-sectional area content of the feed line |
| $S_1$-$S_1$, $S_2$-$S_2$, $S_3$-$S_3$ | Section planes |

The invention claimed is:

1. A cryosurgical instrument (10), comprising:
a hollow shaft including a closed distal end with an outer adhesion surface for harvesting a tissue sample thereon and an expansion chamber disposed within the hollow shaft at the closed distal end thereof;
a feed line (15) disposed within the shaft for supplying a fluid into the expansion chamber (18), wherein the feed line (15) has a capillary line section (21) that extends along a longitudinal axis to a distal end of the feed line, wherein the distal end of the feed line is spaced from the closed distal end of the hollow shaft and terminates at a mouth opening (22) disposed at an endmost distal extent of the feed line (15) in the expansion chamber (18), wherein the mouth opening is spaced from the closed distal end of the hollow shaft and is oriented axially for supplying fluid distally into the expansion chamber;
a return system (19) disposed within the shaft and fluidically connected to the expansion chamber (18) for returning fluid out of the expansion chamber (18);
wherein the feed line (15) has at least a first section (30n-2, 30n-1) and a second section (30n-1, 30n)

proximal to the capillary line section with different-size interior cross-sections (33);

wherein a flow path through the feed line (15) tapers in a form of a funnel in a transition section (32n-2, 32n-1) from the first section (30n-2, 30n-1) to the second section (30n-1, 30n) in a direction of flow (34) of the fluid toward the expansion chamber (18); and wherein the return system includes a return line disposed entirely within the shaft that extends around or adjacent to the feed line and beyond the transition section within the shaft in a direction away from the expansion chamber for returning fluid out of the expansion chamber.

2. The cryosurgical instrument (10) according to claim 1, wherein the flow path in the feed line (15) tapers in the form of a funnel in the transition section (32n-1) toward the capillary line section (21, 30n).

3. The cryosurgical instrument (10) according to claim 1, wherein the feed line (15) has at least two transition sections (32n-2, 32n-1), in which the flow path of the feed line (15) tapers in the form of a funnel in the direction of flow (34).

4. The cryosurgical instrument (10) according to claim 1, wherein the first section (30n-2, 30n-1, 30n) and the second section (30n-2, 30n-1, 30n) are step sections (30n-2, 30n-1, 30n) of a series of at least two step sections (30n-2, 30n-1, 30n) of the feed line (15), wherein—between the at least two step sections (30n-2, 30n-1, 30n) —respectively the transition section (32n-2, 32n-1) is arranged, said transition section being adjacent to the first and second step sections (30n-2, 30n-1, 30n), wherein the interior cross-sections (33) of each step section (30n-2, 30n-1, 30n) belong to an inside cross-section step, wherein the interior cross-sections (33) of an inside cross-section step of a step section (30n-2, 30n-1, 30n) are greater than the interior cross-sections (33) of the inside cross-section step of the step section (30n-2, 30n-1, 30n) adjoining the same transition section (32n-2, 32n-1) in the direction (34) toward the mouth opening (22) of the capillary line section (21) in the direction of flow.

5. The cryosurgical instrument (10) according to claim 1, wherein a flow cross-section of the fluid increases abruptly during a transition from the mouth opening (22) of the capillary line section (21) into the expansion chamber (18).

6. The cryosurgical instrument (10) according to claim 1, wherein the feed line (15) is arranged in or next to the return line (19) of the return system (19), wherein a ratio of a flow cross-section (41) of the return line (19) next to or around the capillary line section (21) with respect to an interior cross-section (33) of the capillary line section (21) is greater than or equal to 5.

7. The cryosurgical instrument (10) according to claim 1, wherein an outside cross-section (40) of the feed line (15) decreases continuously in the funnel-shaped transition section (32n-2, 32n-1) in a direction (34) toward a mouth (22) of the capillary line section (21).

8. The cryosurgical instrument (10) according to claim 1, wherein a section of the feed line (15) having the capillary line section (21) and the transition section (32n-2, 32n-1) are formed in one piece without a seam.

9. The cryosurgical instrument (10) according to claim 1, wherein a section of the feed line (15) having the capillary line section (21) and the funnel-shaped transition section (32n-2, 32n-1) wherein an inside surface of the feed line has a low surface roughness indicative of use of a rotary swaging process.

10. The cryosurgical instrument (10) according to claim 1, wherein a wall thickness of the capillary line section (21) is equal to or greater than a wall thickness of the feed line section adjacent to the transition section (32n-2, 32n-1) toward the capillary line section (21).

11. The cryosurgical instrument (10) according to claim 1, wherein the ratio of an inside diameter (28) of the capillary line section (21) with respect to the length (29) of the capillary line section (21) is between a minimum of 0.004 up to a maximum of 0.2.

12. The cryosurgical instrument (10) according to claim 1, wherein a tapering angle (37) at which the transition section (32n-2, 32n-1) tapers is between 15° at minimum and 40° at maximum.

13. The cryosurgical instrument (10) according to claim 1, wherein the distance (25) between the mouth opening (22) and an opposite wall surface (26) of the expansion chamber (18) is between 0.5 millimeters at minimum and 5 millimeters at maximum.

14. The cryosurgical instrument (10) according to claim 1, wherein an inside diameter (28) of the capillary line section (21) is at most 200 μm.

15. The cryosurgical instrument 10 according to claim 1, wherein the return line (19) is defined by an exterior surface of the feed line (15) and an interior surface of the hollow shaft.

16. A cryosurgical instrument (10), comprising:
a hollow shaft including a closed distal end with an outer adhesion surface for harvesting a tissue sample thereon and an expansion chamber disposed within the hollow shaft at the closed distal end thereof;
a feed line (15) disposed within the shaft for supplying a fluid into the expansion chamber (18), wherein the feed line (15) has a capillary line section (21) that extends along a longitudinal axis to a distal end of the feed line, wherein the distal end of the feed line is spaced from the closed distal end of the hollow shaft and terminates at a mouth opening (22) disposed at an endmost distal extent of the feed line (15) in the expansion chamber (18), wherein the mouth opening is spaced from the closed distal end of the hollow shaft and is oriented axially for supplying fluid distally into the expansion chamber;
wherein an inside diameter (28) of the capillary line section (21) is at most 200 μm;
wherein the ratio of the inside diameter (28) of the capillary line section (21) with respect to the length (29) of the capillary line section (21) is between a minimum of 0.004 up to a maximum of 0.2; and
a return line (19) disposed within the hollow shaft and fluidically connected to the expansion chamber (18) for returning fluid out of the expansion chamber (18), wherein the return line (19) is disposed entirely within the hollow shaft and extends around or adjacent to the feed line in a direction away from the expansion chamber for returning fluid out of the expansion chamber.

* * * * *